US00PP20633P2

(12) United States Plant Patent
Pottschmidt

(10) Patent No.: US PP20,633 P2
(45) Date of Patent: Jan. 5, 2010

(54) GRANDIFLORA ROSE PLANT NAMED 'WEKDOCPOT'

(50) Latin Name: *Rosa hybrida*
Varietal Denomination: WEKdocpot

(75) Inventor: John David Pottschmidt, Cincinnati, OH (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/288,810

(22) Filed: Oct. 23, 2008

(51) Int. Cl.
*A01H 5/00* (2006.01)

(52) U.S. Cl. ..... Plt./132

(58) Field of Classification Search ..... Plt./132, Plt./131, 130
See application file for complete search history.

*Primary Examiner*—June Hwu
(74) *Attorney, Agent, or Firm*—McKee, Voorhees & Seasem P.L.C.

(57) ABSTRACT

A new variety of Grandiflora rose suitable for garden decoration, having flowers of golden yellow edged and blushed with an intense ruby coloration.

1 Drawing Sheet

Classification: The present invention relates to a new *Rosa hybrida* plant.

Variety denomination: The new plant has the varietal denomination 'WEKdocpot'.

BACKGROUND OF THE INVENTION

This invention relates to a new and distinct variety of Grandiflora Rose. The seed parent and the pollen parent of the variety are unknown.

SUMMARY OF THE INVENTION

Among the features which distinguish the new variety from other presently available and commercial rose cultivars known to the inventor are the following combinations of characteristics: its unique flower coloration of golden yellow edged and blushed with an intense ruby coloration, its stipitate glands on the edges of the grooves of the rachis and its red suffusion on the inner surface of the sepals that appears as the flower ages. The plant has an upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKdocpot' may be asexually propagated by cuttings, budding and grafting. The budding and grafting successfully occurred on the plant/rootstock *Rosa hybrida* cv. 'Dr. Huey' (not patented).

COMPARISON WITH PARENTS

The seed parent and the pollen parent of the variety are unknown to the inventor. Accordingly a comparison to the parents is not possible.

COMPARISON WITH THE CLOSEST COMMERCIALLY AVAILABLE CULTIVAR

The new variety may be distinguished from its closest commercially available cultivar, 'BAIpeace' (U.S. Plant Pat. No. 14,731) by the following combination of characteristics: whereas 'WEKdocpot' bears average size flowers (about 6.9 to about 10.0 cm. in diameter) with double petalage (about 27 to 35 petals), 'BAIpeace' bears large flowers (about 13.0 cm. in diameter) with significantly heavier petalage (about 40 petals). The new variety has an upright tall growing habit (about 150 to about 180 cm. in height); whereas the closest commercially available cultivar has a significantly shorter compact and upright growing habit (about 100 to about 150 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

BOTANICAL DESIGNATION

The new variety botanical designation is *Rosa hybrida* 'WEKdocpot'.

FLOWER

The new variety usually bears its flowers singly, sometimes in clusters of two to three per stem. Flowers may be borne in regular rounded clusters on strong medium length stems (about 20 to about 48 cm.). Outdoors, the plant blooms abundantly and nearly continuously during the growing season. The flowers have a moderate tea fragrance.

BUD

The peduncle is about 3.1 to about 7.3 cm. in length, of average caliper (about 0.3 to about 0.4 cm. in diameter), and usually erect. It is almost entirely smooth, with very few stipitate glands. Peduncle color is between 146B and 143A often heavily suffused, especially on the side exposed to the sun, with between 183A and 187B.

Before the calyx breaks, the bud is about 1.3 to about 1.8 cm. in diameter at the widest point, about 1.7 to about 2.2 cm. in length, and moderately ovoid to somewhat pointed in shape. The surface of the bud bears few foliaceous appendages usually with stout much cut foliaceous parts extending beyond the tip of the bud about ¾ or more of its length. Bud color is between 137B and 146B often heavily suffused, especially on the side exposed to the sun, with between 187B and 183A.

The sepals are about 1.9 to about 4.5 cm. in length and about 0.7 to about 1.1 cm. in width at the widest point. The outer surface color of the sepal is between 137B and 146B often heavily suffused, especially on the side exposed to the sun, with between 187B and 183A. The inner surface color of the sepal is near 146B broadly bordered by near 137B. After the sepals open, the inner surface color is often moderately suffused, especially on the area exposed to the sun, with between 187A and 187B. The inner surface of the sepal is covered with fine wooly tomentum; sepal margins are lined with few stipitate glands and numerous hairs.

The receptacle of the flower is of short length (about 0.2 to about 0.4 cm.) and moderately thin in caliper (about 0.5 to about 0.7 cm. in diameter). The receptacle is moderately flat to somewhat urn-shaped in form. Its surface is very smooth with somewhat thin fleshy walls. The receptacle color is between 146C and 143A.

As the petals open (after the calyx breaks), the bud is about 1.9 to about 2.3 cm. in diameter at the widest point, about 2.0 to about 2.5 cm. in length, and ovoid in form. The color of the under surfaces of the newly opened petals is between 14C and 14D often heavily blushed with between 53B and 53C to as dark as between 60A and 187B. There is no visible change in coloration at the point where the petal attaches. The color of the upper surfaces of the newly opened petals is between 17D and 20B often heavily blushed with between 53B and 53C to as dark as between 60A and 187B. There is no visible change in coloration at the point where the petal attaches.

BLOOM

When fully open, the bloom ranges from about 6.9 to about 10.0 cm. in diameter. Petalage is double with about 27 to 35 petals and about 4 to 9 petaloids irregularly arranged. When partially open, the bloom form is moderately globular to somewhat high centered, and the petals are somewhat tightly spiraled to cupped with petal edges slightly reflexed outward. When fully open, the bloom form is cupped, and the petals are loosely cupped with petal edges moderately reflexed to somewhat rolled outward.

PETALS

The substance of the petals is moderately heavy and of medium thickness, with upper surfaces slightly satiny and under surfaces somewhat shiny to matte. The petals are about 2.8 to about 4.2 cm. in length and about 2.3 to about 4.5 cm. in width at the widest point. Petal margins are entire.

The outer petals are broadly rounded to somewhat obovate in shape with rounded apices.

The inner petals are moderately obovate in shape with rounded apices.

Petaloids are about 0.8 to about 2.2 cm. in length and about 0.3 to about 2.3 cm. in width at the widest point. Petaloids are irregularly shaped somewhat obovate to subulate with rounded apices.

NEWLY OPENED FLOWER

The under surface color of the outer petals is between 11D and 155B often heavily blushed with between 63B and 61C to as dark as between 60A and 53A. At the point where the petal attaches, there is a small zone of between 4B and 5C. The upper surface color of the outer petals is between 12D and 155B often heavily blushed with between 58B and 61C to as dark as between 60A and 53A. The blush coloration is usually more intense on the petal edge. At the point where the petal attaches, there is a moderately large zone of between 7C and 6C.

The under surface color of the intermediate and inner petals is between 12C and 18A often moderately blushed near the petal edge with between 53D and 61C. The upper surface color of the intermediate and inner petals is between 14C and 19B often moderately blushed near the petal edge with between 53D and 61C.

The under and upper surface color of the petaloids are similar in coloration to the upper and under surfaces of the intermediate and inner petals.

The general tonality of the newly opened flower is between 14C and 19B often moderately blushed near the petal edge with between 53D and 61C.

THREE-DAY-OLD FLOWER

The under surface color of the outer petals is between 11D and 155B often heavily blushed with between 63B and 58B to as dark as between 60A and 53A. At the point where the petal attaches, there is a small zone of between 4C and 5D.

The under surface color of the intermediate and inner petals is between 11D and 155B often moderately blushed near the petal edge with between 63B and 58B.

The upper surface color of the outer, intermediate and inner petals is between 11D and 155B often heavily blushed with between 61B and 58B to as dark as between 60A and 53A. At the point where the petal attaches, there is a moderately large zone of between 8B and 10B.

The under and upper surface color of the petaloids are similar in coloration to the upper and under surfaces of the intermediate and inner petals.

The general tonality of the three-day-old flower is between 11D and 155B often heavily blushed with between 61B and 58B to as dark as between 60A and 53A.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 110) and are arranged regularly about the pistils; a few are mixed with petaloids. The filaments are of moderately short length (about 0.4 to about 0.7 cm.) most with anthers. Filaments are between 12B and 13B in color. The anthers are of medium size for the class and all open approximately at the same time. Anther color when immature is near 20A on the external part and near 13D on the internal part. Anther color at maturity is near 163C on the external part and near 200B on the internal part. Pollen is sparse and near 16D in color.

FEMALE REPRODUCTIVE ORGANS

Pistils vary in number (average about 125). The styles are moderately uneven, somewhat long in length (about 0.4 to about 0.7 cm.), moderately thin in caliper, and moderately separated to columnar. Stigma color is between 19A and 20A. Style color is between 154C and 150D often moderately blushed near the top with between 53B and 53C. Ovaries are usually all enclosed in the calyx.

Hips have not been observed on this variety when grown in Pomona, Calif.

FOLIAGE

The compound leaves are usually comprised of three to five leaflets and are borne abundantly. The five-leaflet leaves are about 8.3 to about 17.3 cm. in length and about 7.3 to about 14.3 cm. in width at the widest point, moderately heavy to somewhat crisp in texture, and glossy in finish on the upper side and somewhat shiny to matte in finish on the under side. The terminal leaflets are about 4.3 to about 7.7 cm. in length and about 2.8 to about 6.1 cm. in width at the widest point, shaped ovate with moderately acute apices and rounded bases. Their margins are usually simply serrate.

The upper surface color of the mature leaf is between 137A and 141A. The under surface color of the mature leaf is between 147B and 146B. The upper surface color of the young leaf is between 146B and 146A, often heavily suffused with between 187B and 183B. The under surface color of the young leaf is between 138B and 138A, often heavily suffused with between 187C and 183C.

The rachis is average to somewhat heavy in caliper and rough. The upper side is deeply grooved with few hairs and some stipitate glands on the edges of the grooves. The under side of the rachis is rough with few stipitate glands and small prickles. The rachis color is near 146C on the under side and near 146A on the upper side.

The stipules are about 1.1 to about 1.8 cm. in length and moderately wide (about 0.6 to about 0.8 cm.) with long straight points that usually turn out at an angle of more than 45 degrees. The stipule color is between 137B and 138A.

The petiole is average to somewhat heavy in caliper and rough. The upper side is deeply grooved with few hairs and some stipitate glands on the edges of the grooves. The under side of the petiole is rough with few stipitate glands and small prickles. The petiole is about 0.5 to about 1.4 cm. in length and about 0.1 to about 0.2 cm in diameter at the widest point. The petiole color is near 146C on the under side and near 146A on the upper side.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has an upright tall growing habit (about 150 to about 180 cm. in height and about 56 to about 66 cm. spread at the widest point), with full branching. It displays vigorous growth and the canes are of medium caliper for the class (about 1.2 to about 2.1 cm. in width at the widest point).

The color of the major stems is between 147B and 146B. They bear many large prickles that are about 0.8 to about 1.2 cm. in length. The large prickles are angled slightly downward with a moderately long broad oval base; prickle color is between 166D and 164A. The major stem bears few small prickles of similar shape and coloration.

The color of the branches is between 146B and 146A. They bear some large prickles which are of similar shape to the large prickles on the major stems. Prickles are about 0.6 to about 0.8 cm. in length. Prickle color is between 166D and 164A. The branches bear some small prickles of similar shape and coloration.

The color of the new shoots is between 146B and 146C sometimes moderately suffused with between 183A and 187B. They bear some large prickles which are of similar size and shape to the large prickles on the branches. Prickle color is between 153A and 152D often heavily suffused with between 187C and 185A. The shoots bear some small prickles of similar shape and coloration.

I claim:

1. A new and distinct Grandiflora rose plant of the variety substantially as described and illustrated herein.

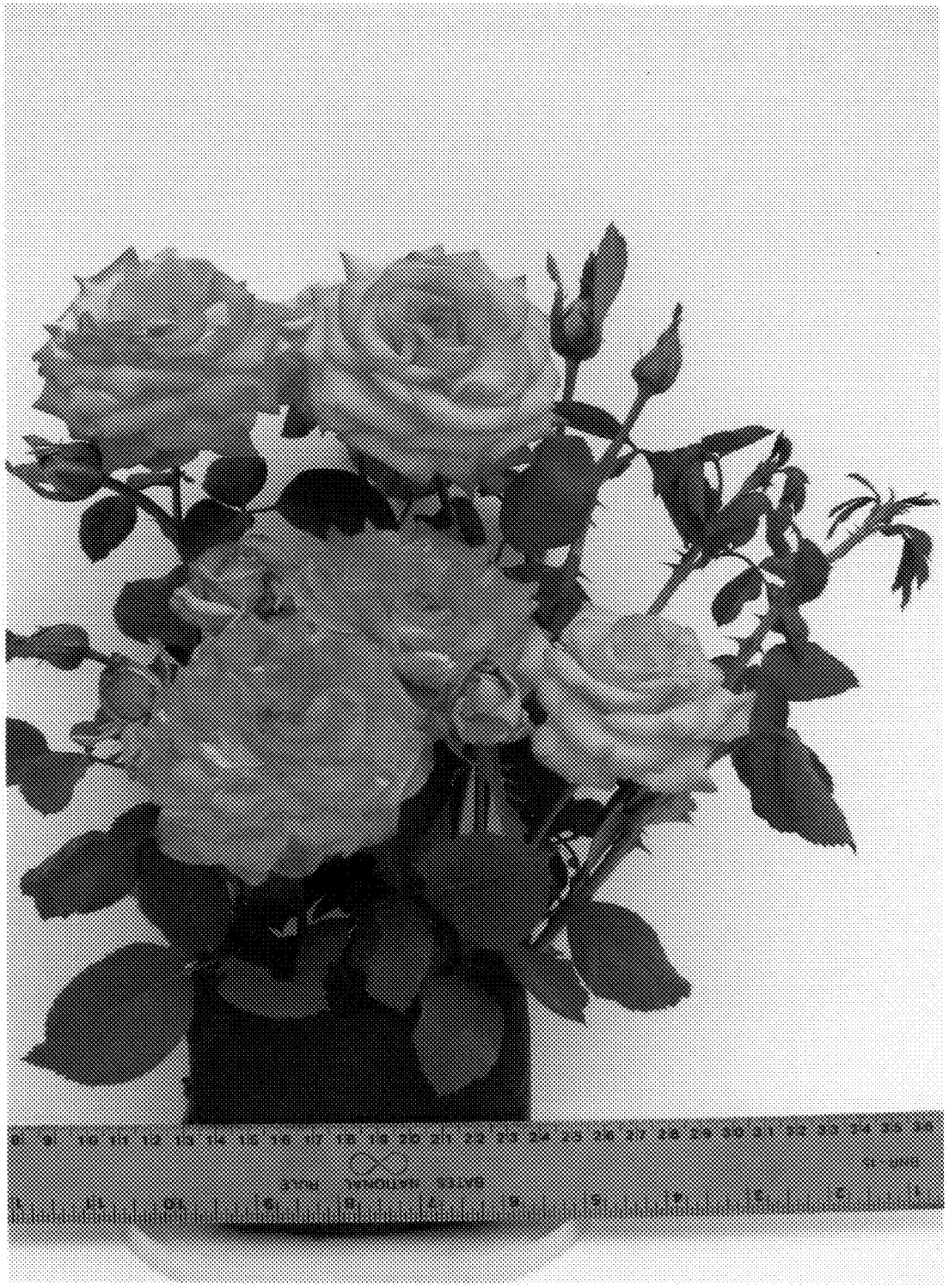

* * * * *